US012636014B2

(12) United States Patent
Alawneh et al.

(10) Patent No.: US 12,636,014 B2
(45) Date of Patent: May 26, 2026

(54) METHOD FOR TREATING SCALP ARTERIOVENOUS FISTULA USING MICRO VASCULAR PLUG

(71) Applicant: Jordan University of Science and Technology, Irbid (JO)

(72) Inventors: Khaled Alawneh, Irbid (JO); Liqaa Raffee, Irbid (JO); Retaj Alawneh, Irbid (JO); Moh'd Al-Barbarawi, Irbid (JO); Hassan Alawneh, Irbid (JO); Majdi Al Qawasmeh

(73) Assignee: Jordan University of Science and Technology, Irbid (JO)

( * ) Notice: Subject to any disclaimer, the term of this patent is extended or adjusted under 35 U.S.C. 154(b) by 198 days.

(21) Appl. No.: 18/328,356

(22) Filed: Jun. 2, 2023

(65) Prior Publication Data

US 2023/0389929 A1     Dec. 7, 2023

Related U.S. Application Data

(60) Provisional application No. 63/348,023, filed on Jun. 2, 2022.

(51) Int. Cl.
A61B 17/12          (2006.01)

(52) U.S. Cl.
CPC .. A61B 17/12109 (2013.01); A61B 17/12159 (2013.01)

(58) Field of Classification Search
CPC ........ A61B 17/12109; A61B 17/12118; A61B 17/12159; A61B 2017/00641; A61B 17/12168
See application file for complete search history.

(56) References Cited

U.S. PATENT DOCUMENTS

| | | | | |
|---|---|---|---|---|
| 6,071,285 A * | 6/2000 | Lashinski | ............... | A61F 2/958 |
| | | | | 606/191 |
| 6,146,373 A * | 11/2000 | Cragg | .............. | A61B 17/12186 |
| | | | | 604/48 |
| 6,454,738 B1 * | 9/2002 | Tran | ........................ | A61L 24/06 |
| | | | | 424/78.37 |
| 9,017,351 B2 * | 4/2015 | Rudakov | .......... | A61B 17/12104 |
| | | | | 606/158 |
| 10,835,258 B1 * | 11/2020 | Pillai | ................ | A61B 17/12109 |
| 2006/0105014 A1 * | 5/2006 | Cruise | ........................ | A61P 9/14 |
| | | | | 424/423 |
| 2006/0263301 A1 * | 11/2006 | Vernon | .............. | A61K 49/0404 |
| | | | | 424/9.4 |
| 2009/0297582 A1 * | 12/2009 | Meyer | ................ | A61B 17/1215 |
| | | | | 156/60 |
| 2014/0236120 A1 * | 8/2014 | Tsai | ................... | A61M 25/0138 |
| | | | | 604/528 |
| 2015/0238306 A1 * | 8/2015 | Marshall | ................. | A61L 31/04 |
| | | | | 623/1.39 |

(Continued)

Primary Examiner — Brooke Labranche
Assistant Examiner — Christina C Lauer
(74) Attorney, Agent, or Firm — Oblon, McClelland, Maier & Neustadt, L.L.P.

(57)          ABSTRACT

A method of treating scalp arteriovenous fistula may include introducing a micro-vascular plug into an affected blood vessel, positioning the micro-vascular plug at a site of a fistula, and securing the micro-vascular plug to occlude blood flow through the fistula. Such a method may also include conducting contrast-enhanced Magnetic Resonance Imaging of a brain to evaluate a scalp mass.

20 Claims, 5 Drawing Sheets

(56)  References Cited

U.S. PATENT DOCUMENTS

| | | | |
|---|---|---|---|
| 2016/0166257 A1* | 6/2016 | Allen | A61B 17/12109 |
| | | | 606/200 |
| 2016/0314601 A1* | 10/2016 | Sankaran | G06T 7/0012 |
| 2018/0235639 A1* | 8/2018 | DeMeritt | A61B 17/12031 |

* cited by examiner

METHOD FOR TREATING SCALP ARTERIOVENOUS FISTULA USING MICRO VASCULAR PLUG

CROSS-REFERENCE TO RELATED APPLICATION

The present application claims priority from the U.S. provisional application number 63/348,023, filed on Jun. 2, 2022, which is incorporated herein by reference.

TECHNICAL FIELD

The present disclosure relates to methods of treatment, and more particularly to methods of treating of Scalp Arteriovenous Fistula using Micro Vascular Plug.

BACKGROUND

Scalp Arteriovenous Fistula ("AVF") is a rare but potentially life-threatening vascular abnormality characterized by the abnormal connection between an artery and a vein within the scalp. The condition can lead to various complications, such as cerebral hemorrhage, high-output cardiac failure, and seizures, and requires prompt diagnosis and treatment.

Current treatment options for scalp AVF include embolization, surgical excision, and ligation of the fistula. While these methods are effective, they can be invasive, time-consuming, and associated with various risks and complications.

The Micro Vascular Plug ("MVP") is a novel, minimally invasive device that has been used in the treatment of congenital heart diseases, pulmonary arteriovenous malformations, and gastrointestinal bleeding.

The device is designed to occlude (block) blood vessels in a controlled manner, providing a minimally invasive alternative to traditional surgical procedures.

The Micro Vascular Plug is composed of a self-expanding nitinol mesh that can be deployed through a microcatheter to the targeted vessel. Once in place, the device expands to fill the vessel, effectively blocking the flow of blood.

SUMMARY

It is an object of the present disclosure to provide a novel method for treatment of scalp AVF. The method involves percutaneous insertion of the MVP into the fistula using a microcatheter under fluoroscopic guidance. The MVP is then deployed to occlude the fistula, leading to the resolution of the abnormality.

It is another object of the present disclosure to provide a method that is minimally invasive in nature, reduced risk of complications, shorter procedural time, and faster recovery compared to traditional treatment methods.

It is another object of the present disclosure to utilize the MVP in the treatment of scalp AVF, which may have the potential to revolutionize the management of this condition, providing a safe, effective, and less invasive alternative to traditional treatment.

The Microvascular Plug represents a novel paradigm with its unique ability to achieve rapid, safe, effective, and permanent vascular occlusion through a single device. It smoothly navigates even tortuous anatomy using a microcatheter; thereby, it is ideally suited to occlude tortuous vessels with which scalp arteriovenous fistula is characterized. Also, the procedure's short duration and its rapid vessel occlusion make this technique a promising tool over other embolic devices, especially in critically ill patients.

Aspects of the present disclosure disclose a method of treating scalp AVF that may comprise introducing an MVP into an affected blood vessel, positioning the MVP at a site of a fistula, and securing the MVP to occlude blood flow through the fistula.

In some aspects of the present disclosure, the method may further comprise conducting contrast-enhanced Magnetic Resonance Imaging ("MRI") of a brain to evaluate a scalp mass.

In some aspects of the present disc disclosure, the method may further comprise inserting a pediatric sheath into a targeted femoral artery directed into a temporal artery, wherein the pediatric sheath may be a 6F short pediatric sheath.

In some aspects of the present disclosure, the method may further comprise introducing a microcatheter with a microwire inside a guiding catheter to reach pseudoaneurysm, wherein the microcatheter may be Rebar-27 reinforced microcatheter.

In some aspects of the present disclosure, the method may further comprise implanting one or more MVPs.

In some aspects of the present disclosure, the method may further comprise placing at least one coil behind the MVPs to prevent their migration.

In some aspects of the present disclosure, the method may further comprise tracking through a tortuous course the microcatheter facilitated by a highly flexible delivery wire and device.

In some aspects of the present disclosure, the method may further comprise holding the highly flexible delivery wire and device in place by oversizing the device to the target vessel diameter, and a partial polytetrafluoroethylene cover to enable rapid occlusion.

In some aspects of the present disclosure, the method may further comprise immersing the MVP device in a bowl containing heparinized saline and withdrawn into a loader catheter by pulling back on the flexible delivery wire until a distal tip of the MVP is fully sheathed.

In some aspects of the present disclosure, the method may further comprise inserting a sheath's distal end into a microcatheter hub positioned in the target blood vessel through a connector.

In some aspects of the disclosure, the connector may be a Y-connector.

In some aspects of the disclosure, the method may further comprise tightening a hemostasis valve.

In some aspects of the present disclosure, the method may further comprise advancing a pusher wire through the microcatheter until a distal platinum marker of the MVP is aligned with a distal marker of the microcatheter.

In some aspects of the present disclosure, the method may further comprise unsheathing the MVP by slowly withdrawing the microcatheter and rotating a nitinol pusher wire in a counter-clockwise direction.

BRIEF DESCRIPTION OF THE DRAWINGS

The disclosure will now be described with reference to the accompanying drawings, without however limiting the scope of the disclosure thereto, and in which.

DETAILED DESCRIPTION

Figure 1:
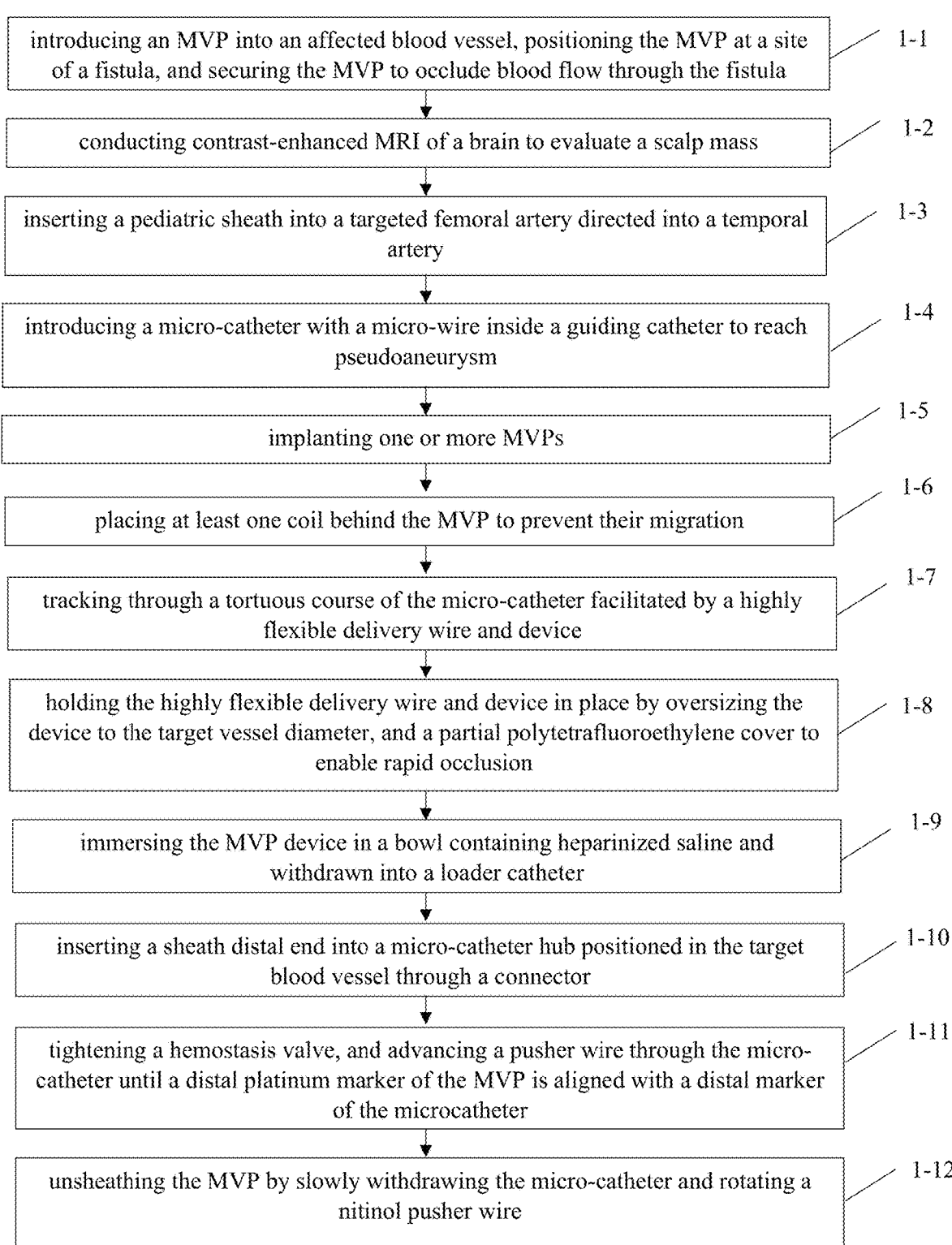
FIG. 1 illustrates a flowchart of a method of treating scalp AVF configured according to embodiments of the present disclosure.

Embodiments of the present disclosure disclose a method of treating scalp AVF. Reference is now being made to FIG. 1, which illustrates a flowchart of a method of treating scalp MVF configured in accordance with embodiments of the present disclosure, the method may comprise introducing a conventional MVP into an affected scalp blood vessel in a patient, followed by positioning the MVP at a site of a fistula, and securing the MVP to occlude blood flow through the fistula (process block 1-1).

In some embodiments of the present disclosure, the method may further comprise conducting a contrast-enhanced Magnetic Resonance Imaging ("MRI") of a brain to evaluate a scalp mass (process block 1-2).

In some embodiments of the present disclosure, the method may further comprise inserting a pediatric sheath into a targeted femoral artery directed into a temporal artery, wherein the pediatric sheath may be a 6F short pediatric sheath (process block 1-3).

In some embodiments of the present disclosure, the method may further comprise introducing a micro-catheter with a micro-wire inside a guiding catheter to reach pseudoaneurysm, (process block 1-4) wherein the micro-catheter may be Rebar-27 reinforced micro-catheter.

In some embodiments of the present disclosure, the method may further comprise implanting one or more MVPs (process block 1-5).

In some embodiments of the present disclosure, the method may further comprise placing at least one coil behind the one or more MVPs to prevent their migration (process block 1-6).

In some embodiments of the present disclosure, the method may further comprise tracking through a tortuous course the microcatheter facilitated by a highly flexible delivery wire and device (process block 1-7).

In some embodiments of the present disclosure, the method may further comprise holding the highly flexible delivery wire and device in place by oversizing the device to the target vessel diameter, and a partial polytetrafluoroethylene cover to enable rapid occlusion (process block 1-8).

In some embodiments of the present disclosure, the method may further comprise immersing the MVP device in a bowl containing heparinized saline and withdrawn into a loader catheter by pulling back on the flexible delivery wire until a distal tip of the MVP is fully sheathed (process block 1-9).

In some embodiments of the present disclosure, the method may further comprise inserting a sheath's distal end into a microcatheter hub positioned in the target blood vessel through a connector (process block 1-10).

In some embodiments of the disclosure, the connector may be a Y-connector.

In some embodiments of the disclosure, the method may further comprise tightening a hemostasis valve, followed by advancing a pusher wire through the microcatheter until a distal platinum marker of the MVP is aligned with a distal marker of the microcatheter (process block 1-11).

In some embodiments of the present disclosure, the method may further comprise unsheathing the MVP by slowly withdrawing the micro-catheter and rotating a nitinol pusher wire in a counter-clockwise direction (process block 1-12).

Figure 2:
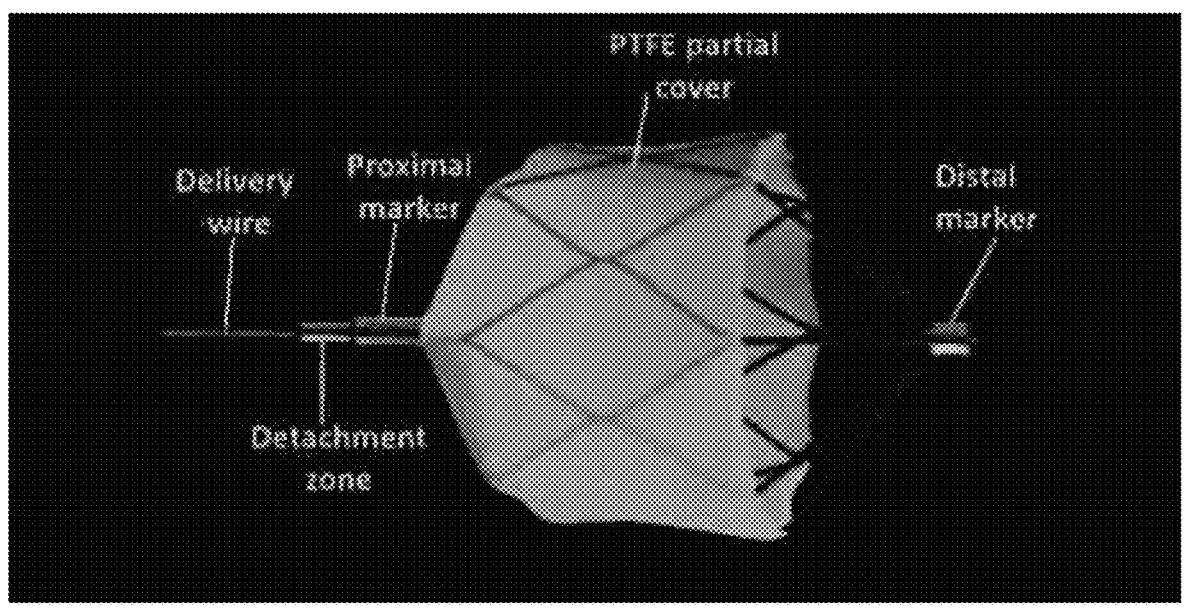
FIG. 2 illustrates parts of a conventional MVP to be used in the method of treating scalp AVF in embodiments of the present disclosure.

Reference is now being made to FIG. 2, wherein the parts of the conventional MVP are shown, including five main parts; the delivery wire, detachment zone, proximal marker, PTFE partial cover and distal marker.

Figure 3A:
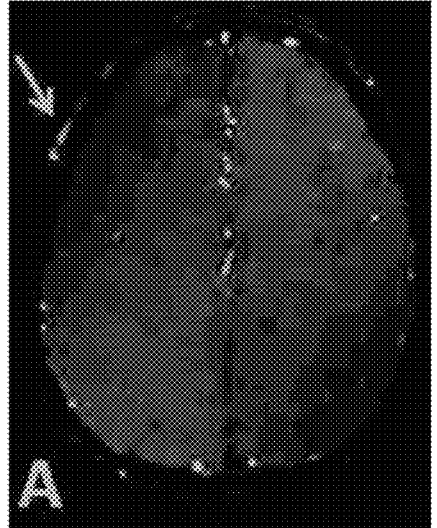
FIG. 3A illustrates a Magnetic Resonance Angiography ("MRA") image of a scalp AVF.
Figure 3B:
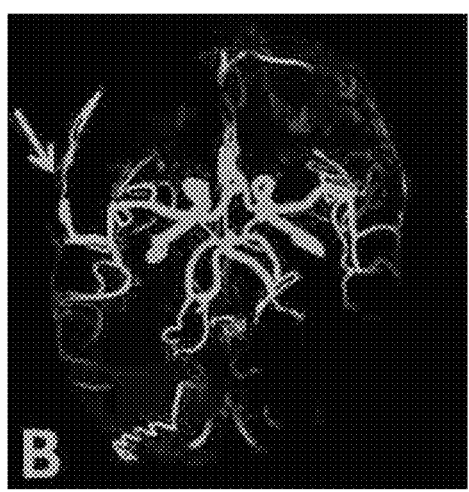
FIG. 3B illustrates an MRA image of a scalp AVF.
Figure 3C:
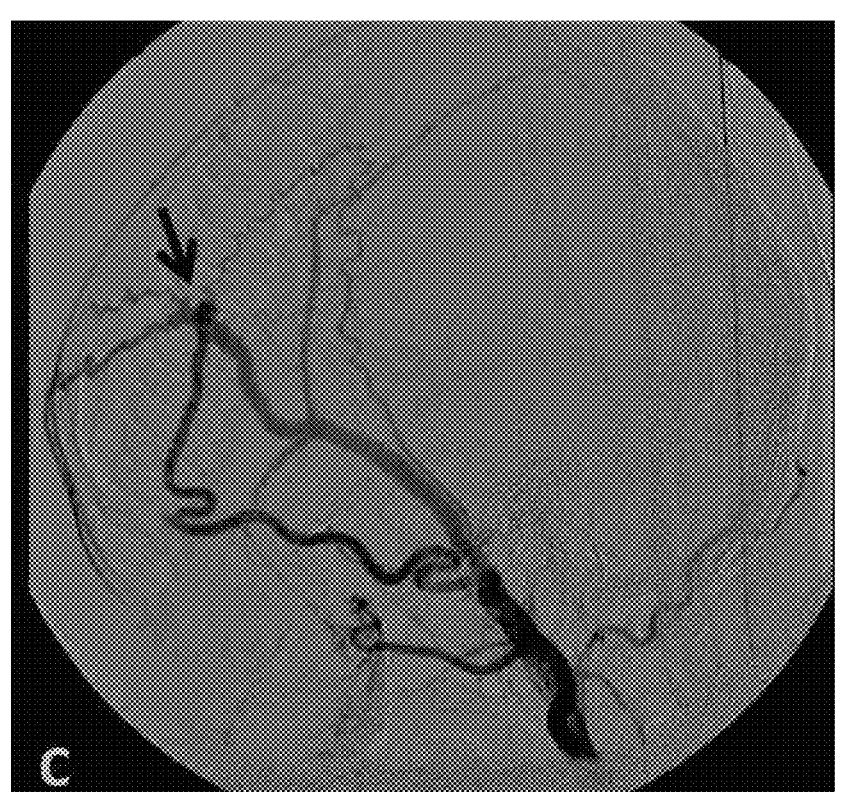
FIG. 3C illustrates a Digital Subtraction Angiography image of the scalp AVF with pseudoaneurysm at the abnormal anastomoses between the right temporal artery and the superior sagittal sinus and the facial vein.

FIGS. 3A-3C show Magnetic Resonance Angiography (MRA), and Digital Subtraction Angiography (DSA) for the scalp arteriovenous fistula with pseudoaneurysm at the abnormal anastomoses between the right temporal artery and the superior sagittal sinus and the facial vein (arrows).

Figure 4:
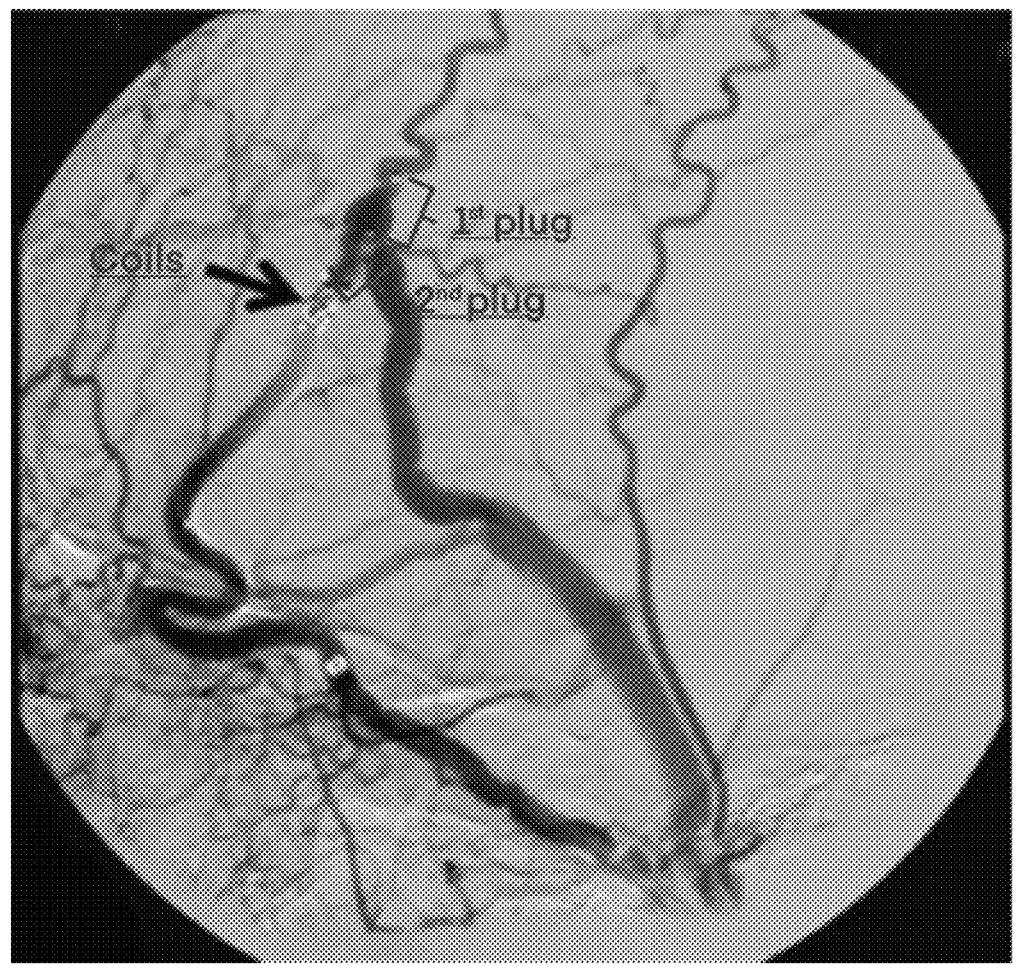
FIG. 4 illustrates the plug marker with coils inside the scalp pseudoaneurysm.

FIG. 4 shows the plug marker with coils inside the pseudoaneurysm.

Figure 5A:
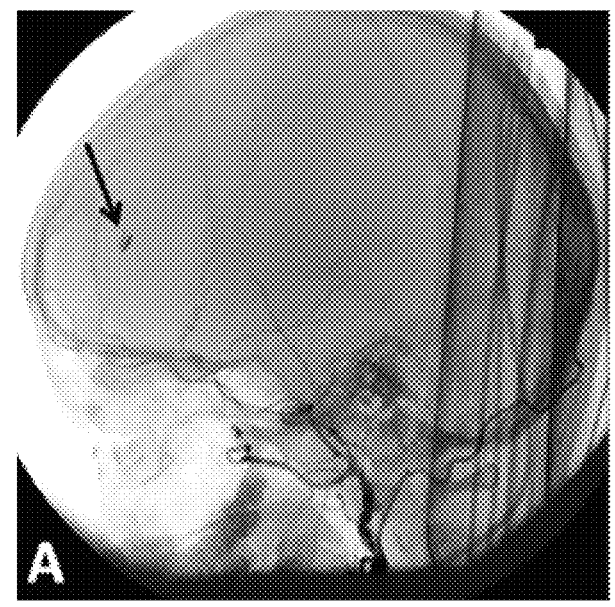
FIG. 5A illustrates Angiography digital image after one week of treatment according to the method of the present disclosure.
Figure 5B:
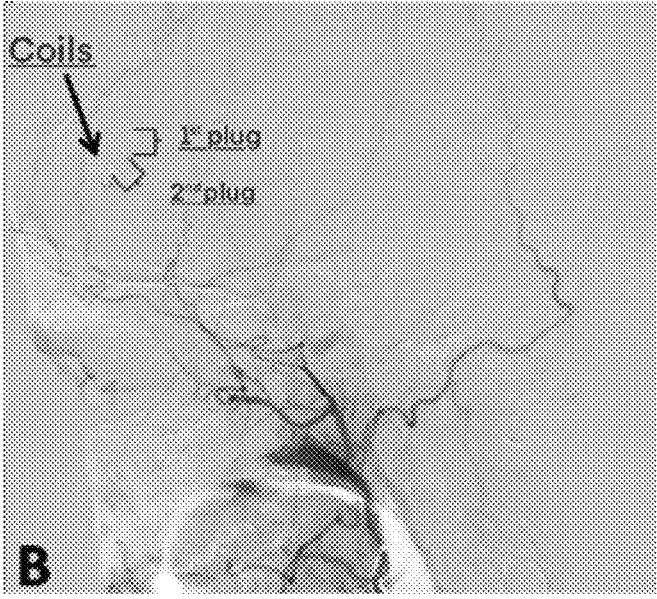
FIG. 5B illustrates Digital Subtraction Angiography after a one year of treatment according to the method of the present disclosure.

FIGS. 5A-5B show the Angiography digital image after one week (A) and Digital Subtraction Angiography (DSA) after one year (B) with an absence of the draining veins at the arterial phase indicating complete occlusion of the fistula. Wherein the arrows show the site of the Microvascular Plug (MVP).

Example 1

Surgical Procedure of Treating Scalp AVF Using MVP

A 10-year-old boy presented to the outpatient clinic complaining of a growing pulsatile mass in the right side of the skull after head trauma six months ago. He had no neurological deficits. Imaging studies revealed scalp AVF with pseudoaneurysm. The arterial feeding was from the right temporal artery, while the blood was drained into the superior sagittal sinus and the facial vein. The fistula was occluded successfully by a Microvascular Plug (MVP). Follow-up angiography one year later showed that the AVF was no longer seen with complete embolization of pseudoaneurysm, total occlusion of the abnormal vessels, and the absence of MVP migration.

The results have shown the first case of successfully using MVP to treat scalp AVF. The MVP is a novel technique with its unique ability to achieve rapid, safe, effective, and permanent vascular occlusion through a single device. Besides, the possibility of delayed-onset traumatic vascular injuries should be considered in a patient with head or facial trauma.

The invention claimed is:

1. A method of treating scalp arteriovenous fistula, the method comprising:

introducing a micro-vascular plug ("MVP") comprising a nitinol mesh and nitinol pusher wire into an affected blood vessel;

positioning the MVP at a site of a scalp arteriovenous fistula in a scalp of a subject; and securing the MVP to occlude blood flow through the scalp arteriovenous fistula with the nitinol mesh.

2. The method of claim 1, further comprising:
conducting contrast-enhanced Magnetic Resonance Imaging of a brain to evaluate a scalp mass of the scalp comprising the scalp arteriovenous fistula prior to the introducing.

3. The method of claim 1, further comprising:
inserting a sheath, attached to the MVP, into a targeted femoral artery directed into a temporal artery through which the MVP is brought into proximity of the scalp arteriovenous fistula.

4. The method of claim 3, wherein the sheath is a 6F short pediatric sheath.

5. The method of claim 1, wherein the introducing further comprises, in mechanical association with the MVP, a micro-catheter with a micro-wire, which are introduced inside a guiding catheter to reach pseudoaneurysm near the scalp arteriovenous fistula.

6. The method of claim 5, wherein the micro-catheter is Rebar-27 reinforced micro-catheter.

7. The method of claim 5, further comprising:
tracking the MVP through a tortuous course of the micro-catheter, towards the scalp arteriovenous fistula, facilitated by a flexible delivery wire and device in mechanical communication with the MVP.

8. The method of claim 7, further comprising:
holding the highly-flexible delivery wire and device, comprising the MVP, in place by oversizing the device to the to a target vessel diameter, and with a partial polytetrafluoroethylene cover to enable rapid occlusion.

9. The method of claim 1, further comprising:
implanting the MVP and optionally one or more further MVPs adjacent the scalp arteriovenous fistula.

10. The method of claim 1, further comprising:
placing at least one coil behind the MVP to prevent their-migration of the MVP and the at least one coil.

11. The method of claim 1, further comprising:
immersing the MVP in a bowl comprising heparinized saline and withdrawing the MVP into a loader catheter, mechanically connected to the MVP, by pulling back a flexible delivery wire of the loader catheter until a distal tip of the MVP is fully sheathed.

12. The method of claim 1, further comprising:
inserting a sheath distal end of the MVP into a micro-catheter hub positioned in the affected blood vessel through a connector.

13. The method of claim 12, wherein the connector is a Y-connector.

14. The method of claim 1, further comprising:
tightening a hemostasis valve in mechanical communication with the MVP and a microcatheter.

15. The method of claim 1, further comprising:
advancing a pusher wire through a micro-catheter, in mechanical communication with the MVP, until a distal platinum marker of the MVP is aligned with a distal marker of the micro-catheter.

16. The method of claim 1, further comprising:
unsheathing the MVP by slowly withdrawing a micro-catheter in mechanical communication with the MVP, and rotating a nitinol pusher wire in mechanical communication to the micro-catheter and the MVP in a counter-clockwise direction.

17. The method of claim 1, wherein, during or after the introducing employs a treatment agent, and
wherein the treatment agent consists of heparinized saline.

18. The method of claim 1, wherein the MVP comprises a partial cover, a proximal marker, and a distal marker.

19. The method of claim 1, further comprising:
introducing a micro-catheter with a micro-wire, in mechanical communication with the MVP, inside a guiding catheter to reach a pseudoaneurysm associated with the scalp arteriovenous fistula; and
placing at least one coil behind the MVP to prevent migration of the MVP and the at least one coil,
advancing a pusher wire through a micro-catheter, in mechanical communication with the MVP, until a distal platinum marker of the MVP is aligned with a distal marker of the micro-catheter,
unsheathing the MVP by slowly withdrawing a micro-catheter in mechanical communication with the MVP, and rotating a nitinol pusher wire in mechanical communication to the micro-catheter and the MVP in a counter-clockwise direction.

20. The method of claim 1, further comprising:
introducing a micro-catheter with a micro-wire, in mechanical communication with the MVP, inside a guiding catheter to reach a pseudoaneurysm associated with the scalp arteriovenous fistula;
holding the flexible delivery wire and device, comprising the MVP, in place by oversizing the device to a target vessel diameter, and with a partial polytetrafluoroethylene cover to enable rapid occlusion;
immersing the MVP in a bowl comprising heparinized saline and withdrawing the MVP into a loader catheter, mechanically connected to the MVP, by pulling back a flexible delivery wire of the loader catheter until a distal tip of the MVP is fully sheathed; and
inserting a sheath distal end of the MVP into a micro-catheter hub positioned in the affected blood vessel through a connector.

* * * * *